US012023667B1

(12) United States Patent
Wilhelm et al.

(10) Patent No.: US 12,023,667 B1
(45) Date of Patent: Jul. 2, 2024

(54) EXTRACTOR FOR CHEMICAL ANALYSIS OF LIPID BIOMARKERS

(71) Applicant: United States of America as Represented by the Administrator of NASA, Washington, DC (US)

(72) Inventors: Mary Beth Wilhelm, Fremont, CA (US); Antonio Joseph Ricco, Los Gatos, CA (US); Morgan James Anderson, Sunnyvale, CA (US); Linda Louise Jahnke, Mountain View, CA (US); Kanchana Uppili Sridhar, Morgan Hill, CA (US); Denise Kathleen Buckner, Cupertino, CA (US); Padraig Michael Furlong, Mountain View, CA (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 0 days.

(21) Appl. No.: 17/336,259

(22) Filed: Jun. 1, 2021

Related U.S. Application Data

(60) Provisional application No. 63/033,205, filed on Jun. 1, 2020.

(51) Int. Cl.
*B01L 3/00* (2006.01)
*G01N 21/65* (2006.01)
(Continued)

(52) U.S. Cl.
CPC ...... *B01L 3/502715* (2013.01); *G01N 21/658* (2013.01); *G01N 30/06* (2013.01);
(Continued)

(58) Field of Classification Search
CPC ....... B01L 3/502715; B01L 2200/0689; B01L 2200/16; B01L 2300/0681; G01N 21/658;
(Continued)

(56) References Cited

U.S. PATENT DOCUMENTS

| 5,948,610 A * | 9/1999 | Ho | C12Q 1/02 436/71 |
| 2006/0163160 A1* | 7/2006 | Weiner | B01D 61/20 106/632 |
| 2014/0305228 A1* | 10/2014 | Witt | B01D 39/00 264/46.4 |

FOREIGN PATENT DOCUMENTS

| EP | 0412004 A2 * | 2/1991 | ............. B02C 18/18 |

OTHER PUBLICATIONS

Ahmida et al Simultaneous determination of plasmatic phytosterols and cholesterol precursors using gas chromatography-mass spectrometry (GC-MS) with selective ion monitoring (SIM). J Chromatogr B Analyt Technol Biomed Life Sci. (Year: 2006).*
(Continued)

*Primary Examiner* — Jennifer Wecker
*Assistant Examiner* — Jonathan Bortoli
(74) *Attorney, Agent, or Firm* — Meredith K. Blasingame; Rhys W. Cheung; Robert M. Padilla

(57) ABSTRACT

A non-aqueous fluidic system for extracting, filtering and concentrating lipid biomarkers from geological samples includes a sample input for receiving a sample, a combined comminution-extraction unit, a filter in fluid communication with the container, and a concentrator operable to receive the solvent phase from the filter and to concentrate lipid extracts for further analysis. The combined comminution-extraction unit has a container into which the received sample is introduced, a port through which one or more organic solvents are introduced into the container for mixing with the sample to thereby extract lipids into an organic phase,
(Continued)

and a comminutor configured to rotate in the container to pulverize the sample to a uniform, reduced particle size and comprising a sonicator configured to agitate and disperse the sample into the one or more organic solvents.

25 Claims, 8 Drawing Sheets

(51) Int. Cl.
    *G01N 30/02* (2006.01)
    *G01N 30/06* (2006.01)
    *G01N 30/72* (2006.01)
    *G01N 33/24* (2006.01)
    *G06N 20/00* (2019.01)

(52) U.S. Cl.
    CPC ......... *G01N 30/7206* (2013.01); *G01N 33/24* (2013.01); *B01L 2200/0689* (2013.01); *B01L 2200/16* (2013.01); *B01L 2300/0681* (2013.01); *G01N 2030/025* (2013.01); *G01N 2030/062* (2013.01); *G06N 20/00* (2019.01)

(58) Field of Classification Search
    CPC .... G01N 30/06; G01N 30/7206; G01N 33/24; G01N 2030/025; G01N 2030/062; G06N 20/00
    USPC .......................................................... 422/502
    See application file for complete search history.

(56) References Cited

OTHER PUBLICATIONS

Jia et al Analysis of Biomolecules Based on the Surface Enhanced Raman Spectroscopy. Nanomaterials (Basel). Sep. 15, 2018;8(9):730. doi: 10.3390/nano8090730. PMID: 30223597; PMCID: PMC6165412. (Year: 2018).*

Acharjee, et al. Integration of metabolomics, lipidomics and clinical data using a machine learning method. BMC Bioinformatics 17 (Suppl 15), 440 (2016). https://doi.org/10.1186/s12859-016-1292-2 (Year: 2016).*

Jesus et al "Comparison of several methods for effective lipid extraction from wet microalgae using green solvent" Renewable Energy, vol. 143, 2019, pp. 130-141, ISSN 0960-1481, (Year: 2019).*

Kim et al. "Enhanced lipid extraction from microalgae in biodiesel production." Hemijska Industrija 71 (2017): 167-174. (Year: 2017).*

* cited by examiner

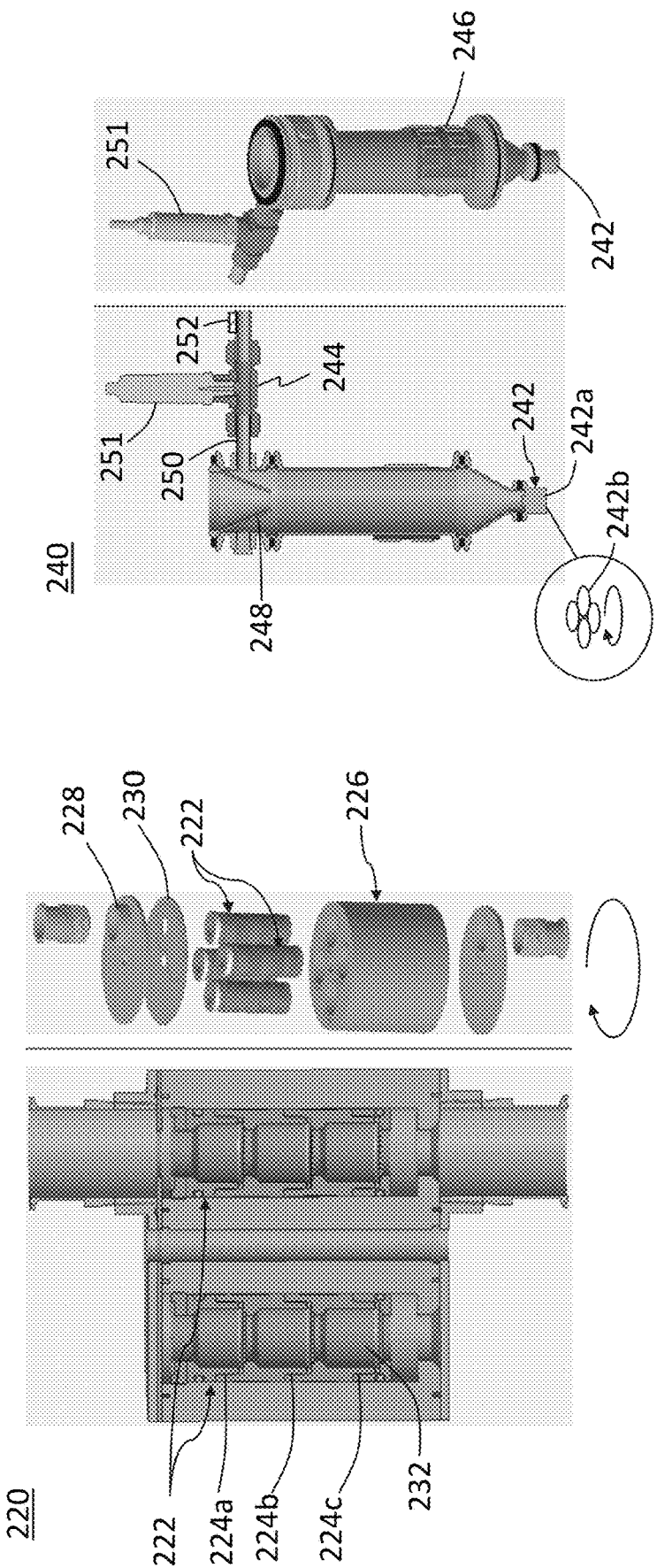

EXTRACTOR FOR CHEMICAL ANALYSIS OF LIPID BIOMARKERS

CROSS-REFERENCE TO RELATED APPLICATIONS

This application claims priority from U.S. Provisional Pat. App. No. 63/033,205, filed on Jun. 1, 2020, the contents of which are incorporated herein by reference in their entirety.

ORIGIN OF THE INVENTION

The invention described herein was made in the performance of work under a NASA contract and by (an) employee(s) of the United States Government and is subject to the provisions of Public Law 96-517 (35 U.S.C. § 202) and may be manufactured and used by or for the Government for governmental purposes without the payment of any royalties thereon or therefor. In accordance with 35 U.S.C. § 202, the contractor has elected not to retain title.

BACKGROUND OF THE INVENTION

Technical Field

The present disclosure relates generally to an autonomous, miniaturized fluidic system for lipid analysis that replicates analytical lab procedures autonomously on a flight-instrument scale.

Description of the Prior Art

Lipids are organic molecules of great interest for astrobiological planetary exploration to the Moon, Mars, and Icy Worlds. In particular, lipids are key molecular targets for future NASA life detection missions to Mars as they can reveal information about life processes and their chemical origin. Lipids are main components of cellular membranes and are therefore essential for terrestrial life and likely required for putative extraterrestrial organisms. Advantageously, lipids are well preserved in the geologic record, some recording the activity of organisms that lived over a billion years ago. They are also synthesized abiotically, and make up about 60% of extractable organics detected in carbonaceous chondrite meteorites.

Lipids, which comprise a broad class of molecules defined by their solubility in organic solvents, can be individually characterized by extraction and analysis using organic solvents of varying polarity. Observation of origin-diagnostic parameters in lipids calls for specific sample processing steps, including (1) sonication of the sample (e.g. icy regolith, crushed rock) with a mixture of non-aqueous (organic) solvents of optimal polarity by lipid class, (2) filtration of mineral residue, and (3) concentration of sample aliquots to increase biomarker signal.

Laboratory techniques for extracting and characterizing lipids are well-established but are laborious, operator dependent, and require large volumes of consumables, precluding in situ implementation on robotic planetary missions. The "gold standard" laboratory protocol steps have yet to be integrated into a single instrument. Current flight approaches to organic characterization utilized by Curiosity's Sample Analysis at Mars (SAM) instrument liberate organics with high temperature thermal extraction (Mahaffy et al., 2012). While flight techniques have successfully detected simple, small organic compounds (Freissinet et al., 2015; Eigenbrode et al., 2018), origin-diagnostic parameters are often obscured or destroyed by high temperatures or gas-phase reactions with mineral/salt byproducts (Sephton et al., 2014).

Proven "gold standard" laboratory techniques for lipid biomarker extraction are laborious, with many opportunities for human error. Additionally, these techniques employ large volumes of consumables and sample material and are consequently unsuitable for flight missions. No single instrument yet exists that is capable of accepting an unprocessed planetary sample, comminuting the sample, extracting lipids, filtering out mineral residue, concentrating the analyte, and delivering the aliquot to analytical instruments for molecular characterization, without requiring intervention from a human operator.

SUMMARY OF INVENTION

The present application presents a solution to the aforementioned challenges, by providing an autonomous, miniaturized fluidic system.

Thus, described herein is an extractor for chemical analysis of lipid biomarkers in regolith. It operates as an autonomous, miniaturized fluidic system, integrating lab techniques for lipid analysis while minimizing reagent volumes and concentrating organics for analysis, thereby increasing signal-to-noise ratios by orders of magnitude. In certain embodiments, the system described herein for astrobiological and life-detection missions (either in situ or sample return) is configured to extract lipid organics from regolith using (1) a fluidic sample processor made of inert materials compatible with organic solvents and (2) a machine-learning system to select processing steps and parameters to maximize lipid yield. A critical gap is bridged by integrating technologies into a system that replicates analytical lab procedures autonomously on a flight-instrument scale with fidelity to original lab techniques. Automated fluidic devices combine controlled handling of liquids with sequential operations and parallelization of replicate processes. By designing such systems to closely interface with both sample-delivery and analytical measurement systems, laboratory analyses are automated.

Also described herein is a fluidic system that extracts and concentrates lipids from approximately 50 grams of regolith, rock, and/or ice using a fluidic and microfluidic sample processor made of materials which are compatible with the non-aqueous organic solvents required for extraction. The disclosed fluidic system can be deployed on a Mars lander/rover to autonomously process a drilled or scooped sample, extract lipids, purify the analyte, and then send the purified sample to a co-manifested downstream analytical instrument, such as a gas chromatograph-mass spectrometer, for further analysis. In certain embodiments, the downstream analytical instrument is in a different location.

Thus, in one embodiment, provided herein is a non-aqueous fluidic system for extracting, filtering and concentrating lipid biomarkers from planetary samples. The disclosed system comprises: (a) a sample input for receiving a sample; and (b) a combined comminution-extraction unit that includes: (i) a container into which the received sample is introduced; (ii) a port through which one or more organic solvents are introduced into the container for mixing with the sample to thereby extract lipids into an organic phase; and (iii) a comminutor configured to rotate in the container to pulverize at least 50% of the sample to a reduced particle size and comprising a sonicator configured to agitate and disperse the sample into the one or more organic solvents, thereby forming a solvent-sample slurry comprising the solvent phase; (b) a filter in fluid communication with the container, the filter operable to pass the solvent phase; and (c) a concentrator operable to receive the solvent phase from the filter and to concentrate lipid extracts for further analysis.

In some embodiments, the filter is a three-stage filter stack.

In some embodiments the reduced particle size is less than 10 μm.

In some embodiments the lipid extracts are concentrated to dryness.

In some embodiments, the disclosed system has a height from about 25 cm to about 120 cm, and a diameter from about 5 cm to about 40 cm.

In some embodiments, the sample size is from about 1 g to about 50 g, and wherein the one or more organic solvent volume is from about 5 ml to about 250 ml. In some embodiments, the sample and the one or more organic solvents are in a v/v ratio of about 1:5 sample to solvent. The one or more organic solvents may comprise one or more of dichloromethane methanol (DCM) and methanol (MeOH).

In some embodiments, the solvent is a 9:1 v:v mixture of DCM:MeOH.

In some embodiments, further analysis comprises one or more of gas chromatography-mass spectrometry, laser-desorption-ionization mass spectrometry, Raman spectroscopy, and surface-enhanced Raman spectroscopy (SERS).

In some embodiments, the sonicator is disposed in intimate contact with the outside of the container and sonic energy is conducted through a wall of said container.

In some embodiments, the comminutor is coupled to a motor exterior of the container using a single shaft penetrating the container through a hermetic shaft seal In some embodiments, one or more sensors for providing one or more temperature or pressure feedbacks are provided.

In some embodiments, the filter stack is one of a plurality of filter stacks disposed in a carousel arrangement operable to rotate and seal different filter stacks into operation.

In some embodiments, the concentrator comprises a removable collection disk to collect and re-dissolve dry lipid extracts.

In some embodiments, the removable collection disk is one of a plurality of disks disposed in a carousel arrangement operable to rotate and seal different collection disks into operation.

In some embodiments, a controller operable to apply a machine learning algorithm to determine resource-efficient processing sequences to maximize extraction yield by the extraction system is provided.

In some embodiments, the machine learning algorithm uses experience data relating to previous expert analysis decisions.

Additionally provided herein is a method for extracting, filtering and concentrating lipid biomarkers from planetary samples, which is performed using the disclosed non-aqueous fluidic system. The method comprises: (i) rotating and pulverizing the sample to a reduced particle size; (ii) adding one or more organic solvents to the sample; (iii) agitating and dispersing the sample into the organic solvents with a sonicator, thereby forming a solvent-sample slurry; (iv) filtering the solvent-sample slurry through a filter stack to obtain a lipid extract; and (v) concentrating the lipid extract for further analysis.

In yet another embodiment, provided herein is a machine-readable storage medium having stored thereon a computer program for extracting, filtering and concentrating lipid biomarkers from planetary samples. The computer program comprises a routine of set instructions for causing the machine to perform the steps of: (i) rotating and pulverizing the sample to a reduced particle size; (ii) adding one or more organic solvents to the sample; (iii) periodically agitating and dispersing the sample into the organic solvents with a mechanical mixer and/or sonicator, thereby forming a solvent-sample slurry; (iv) filtering the solvent-sample slurry through a filter stack to obtain a lipid extract; and (v) concentrating the lipid extract for further analysis.

In some embodiments, concentrating the lipid extract comprises concentrating the lipid extract to dryness to obtain a dry lipid extract, and the method further includes redissolving the dry lipid extract in one or more solvents for the further analysis.

In some embodiments, the method or steps include forwarding the concentrated lipid extract to an analysis system for performing one or more of gas chromatography-mass spectrometry, laser-desorption-ionization mass spectrometry, Raman spectroscopy, and surface-enhanced Raman spectroscopy (SERS).

In some embodiments, the method or steps include applying a machine learning algorithm to determine resource-efficient processing sequences to maximize extraction yield by the extraction system.

In some embodiments, the machine learning algorithm uses experience data relating to previous expert analysis decisions.

The foregoing and other features of the disclosure will become more apparent from the following detailed description of several embodiments, which proceeds with reference to the accompanying figures.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

In the drawings:

FIG. 6 is a sectional elevational view and an exploded view of filtration system 220 in accordance with certain embodiments; and FIG. 7 is a sectional elevational view and isometric view of concentration system 240 in accordance with certain embodiments

DETAILED DESCRIPTION OF INVENTION

Figure 1:
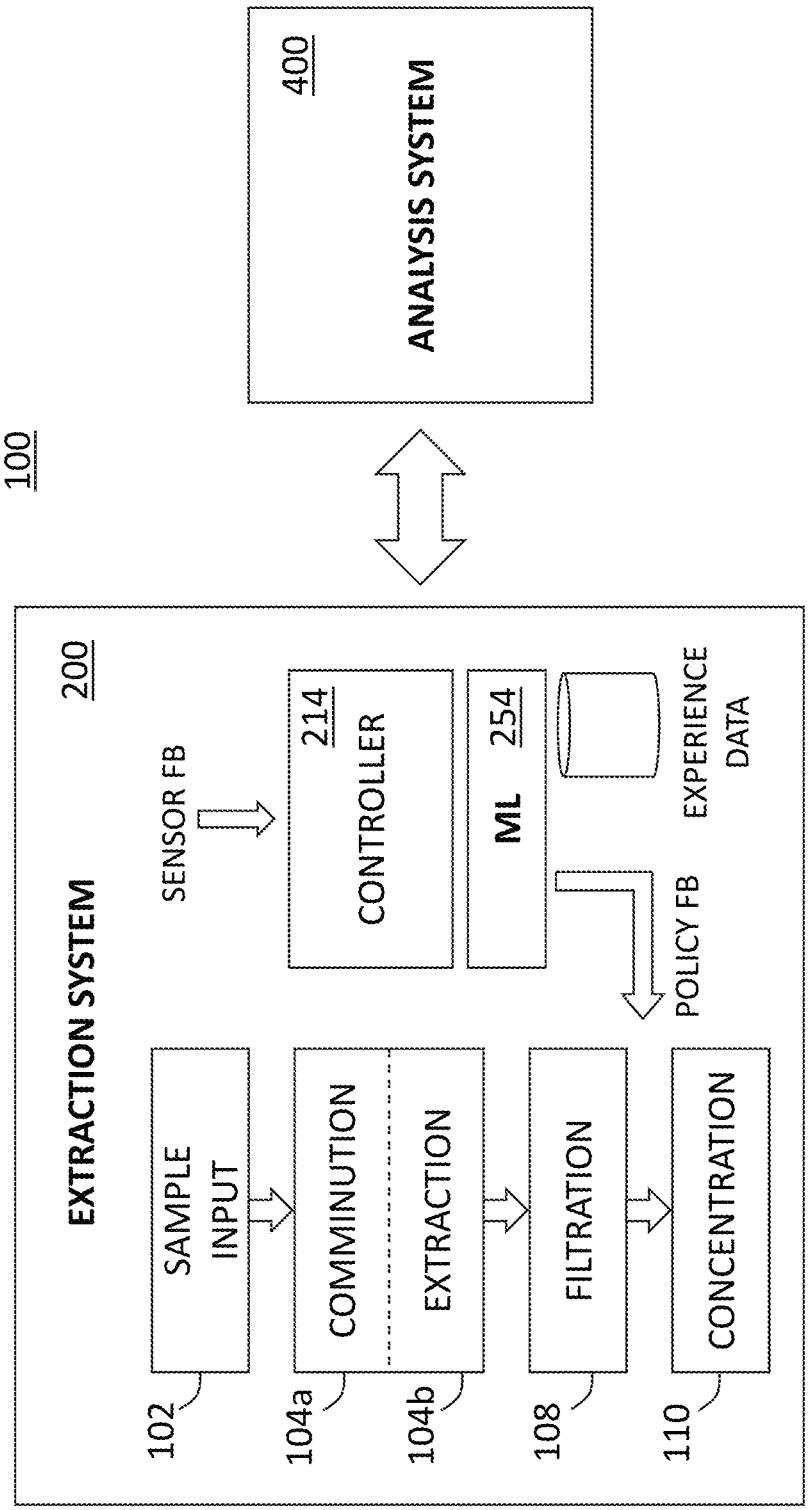
FIG. 1 is a block diagram of a system 100 for determining the presence of lipid biomarkers in a sample such as regolith.

Lipids are a diverse class of organic molecules that are broadly defined by their solubility in non-polar solvents. Lipids encompass fatty acids, phospholipids, glycerophospholipids, sphingolipids, lipopolysaccharides, polyketides, sterols, prenols, triglycerides, diglycerides, and monoglycerides, and have many functions. Triglycerides are stored in adipose tissues as an energy source in both plants and animals. Phospholipids form lipid bilayers and are essential components of biological membranes. Polyketides are synthesized from acetyl and propionyl subunits and find application in the pharmaceutical industry as anti-microbial and anti-cancer agents. Lipopolysaccharides are structural lipids in Gram-negative bacteria. Prenols are antioxidants found in many plants.

On Earth, lipids make up the cell membranes of all known organisms, playing a key role in enabling cellular life. Lipids are also an energy source for organisms and facilitate transport of other biomolecules into and out of the cell. While the majority of lipids on Earth are synthesized by biotic systems, lipids can also be formed abiotically, and are the most abundant freely-extractable organics found in carbonaceous chondrites.

Because lipids can be generated by both biotic and abiotic processes, they contain origin-diagnostic molecular features and patterns, such as chain length, position and number of unsaturated and saturated carbons, position and number of branch points, presence of cyclic moieties and functional groups, and molecule conformation/isomerization. Therefore, examples of biotic and abiotic origin-diagnostic molecular features/patterns can reveal if a group of detected lipid molecules was synthesized via biotic (terrestrial) or abiotic (geologic) processes. These features can be analyzed by solvent extraction and subsequent analysis (e.g., with a gas chromatography-mass spectrometer (GC-MS)). For example, fatty acids synthesized by biotic systems display greater chain length than abiotically synthesized fatty acids. Similarly, other biotic and abiotic lipids display differences in the presence or positioning of double bonds and branch points, presence of cyclic moieties, and molecular conformation. Understanding these patterns and features informs future analyses of expected lipid distributions in samples from life detection targets, such as Mars.

In addition, lipids are characterized by high geological longevity, as they can persist in the terrestrial geologic record for billions of years. Thus, preserved lipids can be excellent indicators of past life in the search for evidence of life on Mars. Extremely arid conditions, like those on Mars over the last three billion years, are likely to enhance structural preservation.

Currently, no single instrument exists that can perform lipid extraction with fidelity as high as benchtop laboratory extraction techniques.

Disclosed herein is fluidic system capable of gathering, purifying and analyzing biological and abiological sources of organic matter, for example that could be found in ancient Martian sediments, for preserved molecular signs of life.

The fluidic system provided herein utilizes sample acquisition and preparation techniques that best conserve the molecular structures and patterns of the samples, analytical techniques customized for biomarkers with highest preservation potential in sedimentary deposits, and distinction between biogenic and abiogenic lipid signatures.

In particular, the disclosed fluidic system makes it possible to process samples in situ, by integrating laboratory extraction steps on a small scale to minimize reagent volumes and by concentrating organics for analysis, thereby increasing detection signal by almost three orders of magnitude. In certain embodiments, fluidic system analyzes about 50 grams of drilled/scooped sample of regolith/rock/ice. The system first comminutes the sample under vacuum to reduce grain size and liberate organics from the mineral matrix. It then cold-traps any released volatile organics for evolved-gas analysis (EGA) while dehydrating. The system then extracts the organic molecules with a series of organic solvents and a sonic probe, and it separates the particulate matter from the lipid analyte. The solvent is evaporated to concentrate the 250 ml sample to (near) dryness, before the system makes the extract available for downstream analytical instruments. Thus, (a) the extract may be transferred in a stream of heated carrier gas of readily volatilized compounds, or (b) redissolved in a defined solvent volume; or (c) the collection vessel may be transferred to the analytical system. These sequential processing steps extract lipids without destroying them or altering origin-diagnostic features before analysis.

The disclosed system adapts best practice laboratory methods for lipid analysis, overcoming analytical challenges like low organic abundance, interference of minerals/salts, and degradation of origin-diagnostic molecular structures. The fluidic system provided herein enables conservation of the origin-diagnostic lipid patterns by maintaining the samples in the liquid phase using organic solvents required for optimal lipid extraction, it reduces signal interference by extracting lipids from the mineral matrix and filtering out minerals, which are known to interfere with Mars sample analysis for example, and it increases the concentration of lipids by about 2,500-fold in the sample relative to initial extract volume. Finally, the fluidic system delivers unadulterated, purified samples to analytical instruments for further analysis.

Example embodiments are described herein in the context of a system for determining the presence of lipid biomarkers in a sample such as regolith. The following description is illustrative only and is not intended to be in any way limiting. Other embodiments will readily suggest themselves to those of ordinary skill in the art having the benefit of this disclosure. Reference will be made in detail to implementations of the example embodiments as illustrated in the accompanying drawings. The same reference indicators will be used to the extent possible throughout the drawings and the following description to refer to the same or like items.

In the description of example embodiments that follows, references to "one embodiment", "an embodiment", "an example embodiment", "certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. The term "exemplary" when used herein means "serving as an example, instance or illustration." Any embodiment described herein as "exemplary" is not necessarily to be construed as preferred or advantageous over other embodiments.

In the interest of clarity, not all of the routine features of the implementations described herein are shown and described. It will be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with this disclosure, the components, process steps, and/or data structures described herein may be implemented using various types of operating systems, computing platforms, computer programs, and/or general purpose machines. Devices of a less general purpose nature, such as hardwired devices, field programmable gate arrays (FPGAs), application specific integrated circuits (ASICs), or the like, may also be used without departing from the scope and spirit of the inventive concepts disclosed herein. Where a method comprising a series of process steps is implemented by a computer or a machine and those process steps can be stored as a series of instructions readable by the machine, they may be stored on a tangible medium such as a computer memory device (e.g., ROM (Read Only Memory), PROM (Programmable Read Only Memory), EEPROM (Electrically Eraseable Programmable Read Only Memory), FLASH Memory, Jump Drive, and the like), magnetic storage medium (e.g., tape, magnetic disk drive, and the like), optical storage medium (e.g., CD-ROM, DVD-ROM, paper card, paper tape and the like) and other types of program memory.

Herein, reference to a computer-readable or machine-readable storage medium encompasses one or more non-transitory, tangible storage media possessing structure. As an example and not by way of limitation, a computer-readable storage medium may include a semiconductor-based circuit or device or other IC (such, as for example, a field-programmable gate array (FPGA) or an ASIC), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. Herein, reference to a computer-readable storage medium excludes any medium that is not eligible for patent protection under 35 U.S.C. § 101. Herein, reference to a computer-readable storage medium excludes transitory forms of signal transmission (such as a propagating electrical or electromagnetic signal per se) to the extent that they are not eligible for patent protection under 35 U.S.C. § 101. A computer-readable non-transitory storage medium may be volatile, nonvolatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

In accordance with certain embodiments, an autonomous, non-aqueous fluidic system capable of extracting lipid biomarkers from planetary samples, performing filtration of the resulting aliquot, and chemically preparing targets for downstream analysis through a series of processing steps is enabled and described. In certain embodiments, these steps include: (1) comminution of a soil, dirt, or regolith sample (~10 g) to a particle size of about 0.5 micron; (2) Addition of about 10 mL a sequence of organic solvents with decreasing polarity including methanol, dichloromethane, and hexane; (3) Sonication and mixing of sample with the solvent using magnetic microbeads; (4) Filtration of mineralogical component >about 0.2 micron in size leaving behind only organic solvent containing biomarkers of interest in about 10 s of mL of solvent; (5) Concentration of solvent containing biomarkers to about 100 microliters in volume; (6) derivatization or thermochemolytic preparation of aliquot for analysis with a chromatography-mass spectrometry type analytical instrumentation (e.g., GC-MS, LC-MS); (7) Reporting analysis results to local spectral library, iterating on next analysis step using machine learning. In certain embodiment, the instrument for performing the described analysis is constructed out of material that is inert to organic solvents including anodized aluminum, silica, glass, and/or stainless steel.

Currently, no single instrument exists that can perform the aforementioned steps 1-7 for lipids. Instead of using a high-temperature oven to extract lipids, the system in certain embodiments replicates a laboratory approach in a scaled-down single instrument that is suitable for deployment in a spacecraft lander on a planet or other extraterrestrial body. It will facilitate actualization of science-enabling objectives by (1) conserving origin-diagnostic lipid structures/patterns by maintaining them in the liquid phase, (2) reducing signal interference by extracting lipids from the mineral matrix and filtering out minerals, and (3) increasing the concentration of lipids by about 1000× in the sample sent to downstream analytical instrumentation. Achieving these three science-enabling objectives will increase chances of life detection in an astrobiologically significant sample in missions to Mars, Enceladus, and/or Europa for example.

In certain embodiments the system described herein overcomes three primary challenges to adapt it for a spacecraft system to produce a concentrated aliquot compatible with downstream analytical instrumentation.

Use of Non-Aqueous Solvents and Weak Acids: The non-aqueous solvents that are required to solubilize lipids would degrade polymers previously utilized in spacecraft aqueous fluidic systems.

Low Biomass and Analytical Instrument Limits of Detection (LOD): Measuring organics low in abundance in planetary samples is a key life detection challenge (Summons et al., 2011). For example, the most organic-poor Mars-analog soil samples from the Atacama Desert have a concentration of fatty acids of 20 femtomole-120 picomole per gram of soil (Wilhelm et al., 2018). The limit of detection of the SAM GC-MS is in the picomole range (Mahaffy et al., 2012). Thus, lipids contained in samples with concentrations less than the LOD will have to be concentrated by orders of magnitude in order to be detected. Additionally, implementation of contamination control of residual organics (e.g. Planetary Protection Category IVb or IVc) is important to prevent false positives.

Preparation for the Planetary Environments: Planetary samples are expected to contain complex organics associated with an unknown mineral matrix. In certain embodiments, bonds of lipids with other organic and inorganic compounds need to be broken. Small sample masses (~grams of ice or regolith) presented to an analytical suite, for example introduced by a drill or scoop, could be easily coupled to the front end of the instrument herein, which will then process this material and present it to downstream instrumentation for analysis.

FIG. 1 is a block diagram of a system 100 for determining the presence of lipid biomarkers in a sample such as regolith in accordance with certain embodiments. The system 100 includes an extraction system 200 that optimizes solvent extraction and concentration of lipids from regolith, rock powder, or icy materials for delivery to an analysis system 400, which may include instruments for molecular characterization and analysis. In certain embodiments, regolith, rock powder, or icy material may be sourced from earth, for example for use in the field of oil exploration or contamination detection, or from non-terrestrial bodies such as planets, moons, and other life-detection targets in space exploration.

Figure 3:
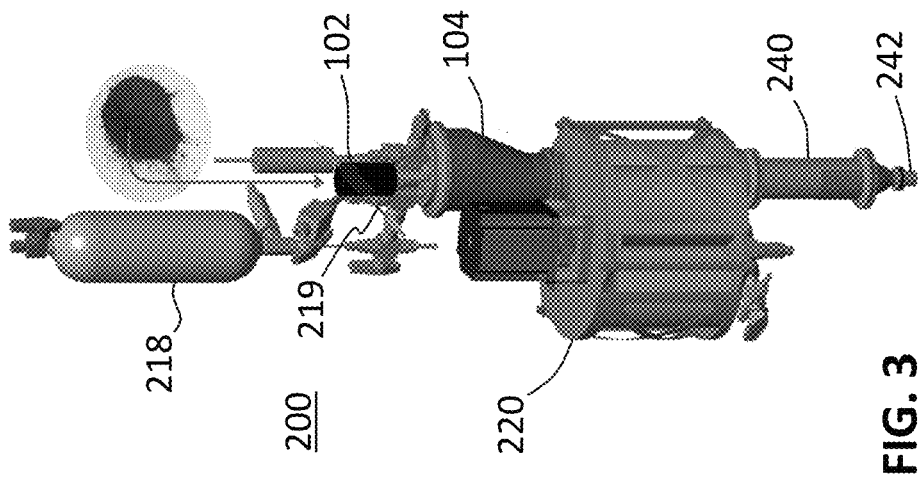
FIG. 3 a more detailed view of an implementation of the system 100 in accordance with certain embodiments.
Figure 2:
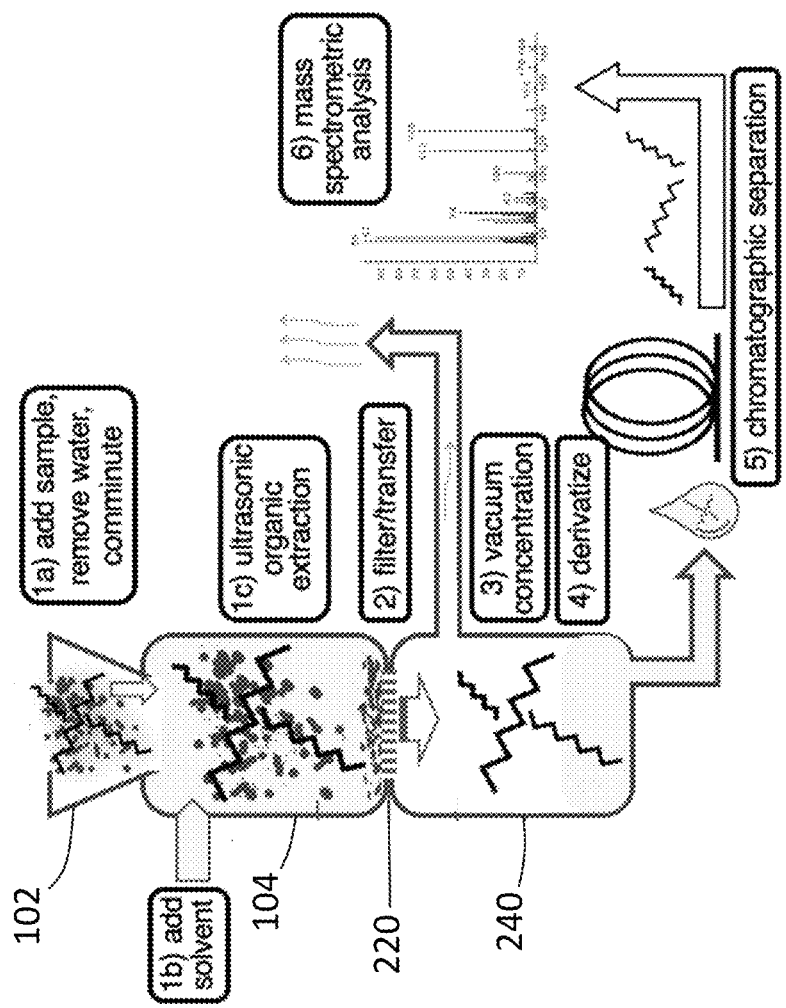
FIG. 2 is a schematic diagram of the system 100 of FIG. 1.

With additional reference to FIGS. 2 and 3, which show extraction system 200 schematically and in greater implementation detail, respectively, a sample input unit 102 is used to introduce a sample, for example regolith, into the extraction system 200. The sample input unit 102 may be a sealable opening or port, for example in the shape of a funnel or tube to help direct the regolith sample into the extraction system. In certain embodiments, the quantity of sample introduced through unit 102 is about 50 grams.

The introduced regolith is subjected to comminution and extraction, for example in comminution unit 104a and extraction unit 104b, which units may be physically combined together as a single comminution-extraction component or chamber (collectively referred to as comminution-extraction unit 104) that is configured to perform both of these processes, as denoted by the broken line in FIG. 1. A considerable savings in weight, volume and energy are some of the advantages of combining these two functionalities using comminution-extraction unit 104, and this is particularly important for spaceflight and for mobile applications.

Figure 4:
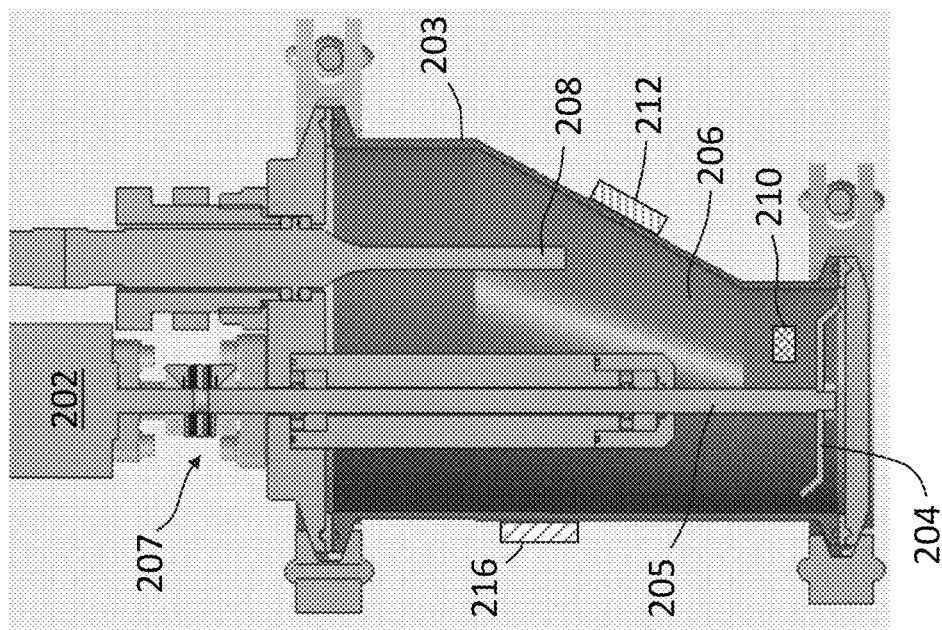
FIG. 4 is a sectional elevational view of comminution-extraction unit 104 in accordance with certain embodiments.

A more detailed view of comminution-extraction unit 104 is shown in FIG. 4. Comminution-extraction unit 104 is generally in the form of a container 203 defining a chamber 206 into which the regolith is introduced. Comminution in the unit 104 is performed using a rotatory mechanism to provide (1) space-efficient means for pulverization and (2) rotation-induced flow to achieve particle size uniformity and increase surface area available for extraction by reducing the particle size of the sample. Alternate comminution strategies contemplated include pin milling, disk milling, and ball milling. In certain embodiments, comminution to a particle size distribution (PSD) such that 50% of the particles are less than about 15.6 μm in diameter is preferred.

Comminution-extraction unit 104 includes a motor 202 that operates in a first mode to spin a comminutor 204, for example a blade, at a prescribed speed sufficient to pulverize the sample to a desired PSD. In certain embodiments, at least 50% of the sample is pulverized to a reduced sample size. In certain embodiments, the first mode motor speed is for example about 28,000 rpm. Such a blender-style comminutor design, in which the reach of the motor is extended by a shaft 205 coupling it to comminutor 204, is advantageous for two reasons. First, it is smaller and lighter than many other comminutor designs, allowing the comminutor to fit inside chamber 206 alongside a sonicator probe 208 as discussed below. Second, this design only requires a single shaft 205 to penetrate the chamber to couple the comminutor to an exterior motor, so a hermetic seal can be maintained using a rotary shaft seal 207. These two aspects of the blender-style comminutor design allow the comminution and extraction chamber to be combined, reducing volume, mass, and complexity of the overall system. Additionally, the comminutor 204 can act, in a second mode, as an agitator at lower rotational speed to keep particles suspended in solvent and circulating past the sonicator probe 208 during extraction.

Figure 5:
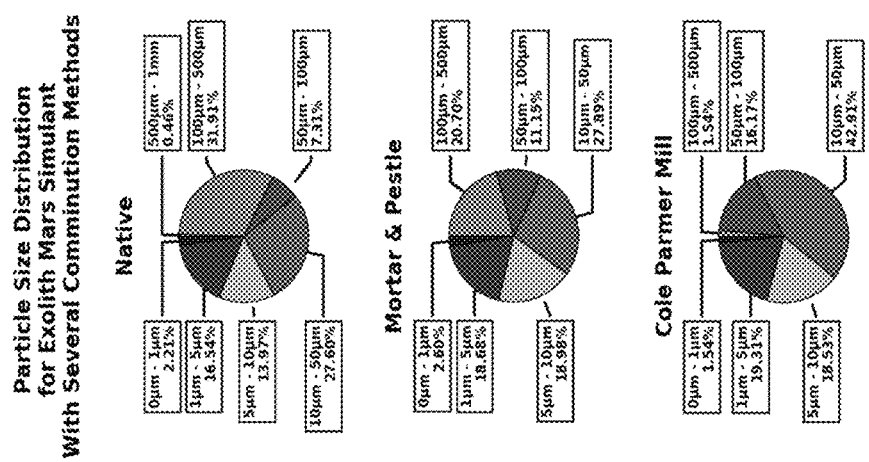
FIG. 5 is a graph showing particle size distribution (PSD) of "native" Exolith Mars soil simulant compared to simulant comminuted via traditional laboratory mortar and pestle and using a Cole Parmer™ mill.

A comparison between comminution methods for Exolith Mars soil simulant is shown in FIG. 5, demonstrating that a rotary type comminutor in accordance with the invention, such as that provided by Cole Parmer™, comminutes sample to a finer particle size than traditional mortar and pestle techniques. The finer particle size achieved matches or increases lipid extraction efficiency over traditional laboratory techniques. In certain embodiments, to perform comminution, the sample is first introduced into the chamber 206 dry and the comminutor 204 is rotated at about 28,000 rpm to reduce particle size through repeated high-velocity impacts. To prevent the comminutor from excessively heating the sample via friction, internal chamber temperature can be monitored, and the comminution process stopped periodically or slowed if necessary to allow the sample to cool. One or more temperature and/or pressure sensors 210 can be provided internally or externally of the chamber 206 to provide temperature and pressure sensor feedback.

Comminution-extraction unit 104 also performs extraction, which may be initiated by introducing solvent into the chamber 206 while the comminutor 204 operates as an agitator, rotating at a lower speed to maintain particle suspension. Agitation and mixing of the regolith sample allows disaggregation to expose lipids to a nonpolar solvent. In certain embodiments, a non-aqueous organic solvent cocktail is selected with polarity tuned to solubilize the lipids of interest: a 9:1 v/v ratio of dichloromethane (DCM) to methanol (Me-OH), for example, constitutes the organic phase into which the lipids are dissolved.

In certain embodiments, optional immersible probe sonicator 208 is utilized to enhance lipid extraction. Sonication, which can be applied in addition to or in lieu of mixing/stirring with the comminutor 204, aids in dispersing solids in a sample, penetrates through a specific particle size range via sound energy at specific frequencies, and sufficiently solubilizes lipids of interest that may be interacting molecularly with minerals or trapped in mineral cracks. In addition, immersible sonication probe 208 improves homogenization effectiveness. In certain embodiments, a custom sonic horn 208 that sonicates at 10-110° C., along with a custom low-volume sealed probe mount is used. In certain embodiments, to avoid the use of high-speed rotary solvent seals, an alternative approach using non-immersible side sonication may be used. Side sonication can use an ultrasonic transducer 212 that resides on the outside surface of container 203 in intimate contact with its walls. The container walls thus conduct sonic energy into the chamber 206. Chamber pressure and temperature can be controlled, using suitable sensors 210 providing sensor feedback to a controller 214 (FIG. 1), for example to maintain lipid integrity.

As mentioned above, sonic energy dissipated into the slurry raises the temperature and pressure in the chamber 206. In certain embodiments, for example assuming that the external environment is ambient Martian conditions for daytime operations in the northern lowlands, then to prevent solvent evaporation, the processing system 200 must be closed. The pressure and temperature sensors 210 monitor chamber conditions to protect the sample, prevent solvent boiling, and ensure optimal sonic transducer function. Controller 214 can be programmed to turn the sonicator off when temperature approaches a prescribed threshold, for example 110° C., and heat will dissipate through the chamber walls until internal conditions are appropriate to resume sonication.

In certain embodiments, the temperature of the sample and solvent may need to be raised, for example to about 10° C., before starting the sonic probe. For this purpose or other purposes, heaters 216 can be installed, for example externally to the sample chamber 206. Prior to dispensing into the chamber 206, solvent can be stored in an appropriate solvent-resistant container, for example a stainless steel Swagelok™ pressure vessel 218 in fluid communication with the chamber 206 by way of a sealable port or valve 219. In certain embodiments, dispensed solvent quantity may be tracked, for example using a contactless liquid level meter (not shown) installed in the top of the chamber 206 or in vessel 218 to control dispensed volume by controller 214. Because the solvent vessel 218 and dispenser valves may be in contact with the solvent much longer than other portions of the system, material compatibility and lifecycle testing plans of these parts may be particularly important.

Once lipids are extracted from soil particles into the solvent phase, filtration is used to isolate solvent from soil. In accordance with certain embodiments, this is accomplished by filtration unit 108 (FIG. 1). Various contemplated filtration methods include centrifugal, membrane, depth, and tangential-flow. In certain embodiments, the preferred design implements membrane pressure filtration, described with reference to FIG. 6, to achieve high-purity material or product. As solvent-particulate slurry flows through the filtration system 220 from chamber 206 of comminution-extraction unit 104, the filter membrane(s) retains particulates on its surface (the retentate) and allows passage of the solvent and extracted lipids (the permeate), as detailed below.

Filtration system 220 comprises stacks 222 of three filters 224a, 224b, 224c (collectively filters or filter cartridges 224) that are arranged in the flow direction in order of decreasing pore size. As shown, four filter stacks 222 are arranged in a rotating carousel 226 in certain embodiments. The number of filter stacks and filters per stack may be different than that described in this example arrangement. Using the carousel arrangement, samples may be processed in sequence, one filter stack at a time, the filters stacks being rotated into position for each different sample. During extraction, carousel ports 228 to the filter stacks are closed, for example by rotating a disk 230 to a closed position preventing flow of material into the filter stack. Each filter stack 222 is composed of custom, modular filter cartridges 224 which house one filter membrane 232 of a unique pore size. Membranes are selected to encompass the sample PSD. In accordance with certain embodiments, DCM-compatible materials are used for membranes, sealing, and housing. In certain embodiments, membranes 232 include porous PTFE sheets and stainless-steel mesh screens (not shown), and O-ring seals (not shown) are composed of Viton-A™ and PTFE or Kalrez™.

Due to reduced gravity on Mars or other non-terrestrial bodies, particle sedimentation velocities cannot be assumed similar to those on Earth (Kuhn et al., 2014; Managadze et al., 2017). To circumvent this issue and aid the filtration process, a pressure differential may be applied across the filter membranes 232. Since the system is closed, solvent will approach its vapor pressure at a given temperature—this is the "upstream" pressure. Temperature within each filter stage is a function of both heat generated during previous comminution and extraction steps and active heating applied to each filter stage to provide closed-loop control of the vapor pressure on the upstream side of each filter. In certain embodiments, a downstream vacuum will be applied in the concentrator subsystem (described below) to enhance the differential pressure and, consequently, flow through the filter stack 222.

Generally, filtration throughput is a function of effective filtration area, pore size, and applied differential pressure. Since very high yield is desired (target removal of >90%/45 g of soil particles from solvent phase and retention of >85%/210 mL of solvent per sample) and comminution produces a heterogenous distribution of particle sizes, a series of decreasing pore-size membrane filters 224 may be used. The solvent-particulate slurry flows through the porous membrane sheet 232 that rejects particulates larger than its pore size. To minimize potential clogging from build-up of a filter cake on top of the membrane, a large, effective filtration area of the membrane is used in certain embodiments. This is balanced with potential increase in fluid retention in the membrane for an increased filter diameter. In certain embodiments, series filtration may be single-sample use only, as there may not be an automated mechanism for recovering the filter cake from a membrane surface, so multiple sequential filtration stacks 222 are implemented for multi-sample use. In certain embodiments, this is accomplished using the carousel arrangement shown.

Membrane pressure filtration as described herein may be most suitable in certain embodiments for its simplicity and lower energy requirements. Other separation techniques are also contemplate. While pressurized filtration may place more stress on a system, implementation of vacuum filtration alone is typically used for capture of the solid phase (vs. liquid phase) and is less suitable for low-boiling point solvents. Centrifugation, while efficient at separating particulate and solvent phases, necessitates a complicated mechanism for removal of the supernatant solvent. Depth filtration enables entrapment of a large quantity of particulates without clogging; however, recovery of the particulates for further analysis is difficult. Tangential-flow filtration yields high purity permeate but necessitates a pumping mechanism for fluid circulation, ergo high energy consumption and added complexity.

After filtration 108 (FIG. 1), a concentration stage 110 is implemented. Sample flows down from the filter stack 222 into a concentrator 240, shown in greater detail in FIG. 7, for collection in an analysis assembly 242. This assembly may be simple cup 242a, or a disk 242b, or a carousel arrangement of movable cups or disks, similar to the filter stacks above, so that multiple collections can be performed. The internal fluid path is designed to minimize flow discontinuities, and materials are selected to minimize non-specific binding of sample on internal surfaces. A regulated vent 244, for example to Martian atmosphere (6-7 mbar), depressurizes the chamber and volatizes the light organic solvent carrier away from heavier lipid extracts of interest. In certain embodiments, temperature is controlled via external heaters 246. In one example, a 250 mL dilute solution reduces to a 100 µL lipid analyte solution by slow vacuum concentration (2500× concentration) to avoid losing solutes in aerosols.

Vacuum concentration uses the ambient climate to reduce energy inputs. Applying vacuum through vacuum concentrator 251 and regulated vent 244 vaporizes the solvent, for example the DCM, and lipids/hydrocarbons concentrate in the solution as the DCM vapor fraction diffuses out of the system. Application of heat maintains temperature within the chamber by offsetting latent heat loss. Other methods of concentration, such as distillation and centrifugation, are contemplated, but they may require both heating and cooling inputs or energy expenditures for mechanical actuation. Vacuum concentration using vacuum concentrator 251 and regulated vent 244 is advantageous for simplified, low-energy solvent removal, especially when processing volatile organic solvents. In certain embodiments, the vacuum concentrator 251 consists of interchangeable NW-50 Kwik Connect™ components. A funnel-shaped nozzle 248 is mounted in the 2-port adapter to direct solvent flow away from the vacuum line 250. A temperature and/or pressure sensor 252 measures heat losses of the bulk sample solution, providing its output to controller 214 to adjust thermal inputs and control evaporation rates. Inline pressure sensing provides sensor feedback control in conjunction with pressure systems in the filter stage mounted above. In certain embodiments, a salt removal procedure (not shown) may be added to the process flow. In certain embodiments, the concentrator 240 design has a unibody construction that mounts directly to the filter stage 220.

After the lipid sample is obtained from extraction system 200, it is analyzed in analysis system 400. This may include chromatographic separation using gas chromatography (GC), or mass spectrometry (MS) analysis, or both. In certain embodiments mating features (not shown) complementary to a GC-MS analytical instrument, such as a SAM-like GC-MS analytical instrument, may be provided. Of course other types of analysis are contemplated, in lieu of or in addition to GC-MS, including but not limited to laser-desorption-ionization mass spectrometry, Raman spectroscopy, and surface-enhanced Raman spectroscopy (SERS).

In certain embodiments, chemical reaction(s) of the sample and/or the extract may be performed, for the purpose of extracting a larger amount of the organic material from the sample, or for the purpose of making the extracted lipids more amenable to analysis (e.g. to make the non-volatile ones volatile enough for GC-MS).

Figure 10:
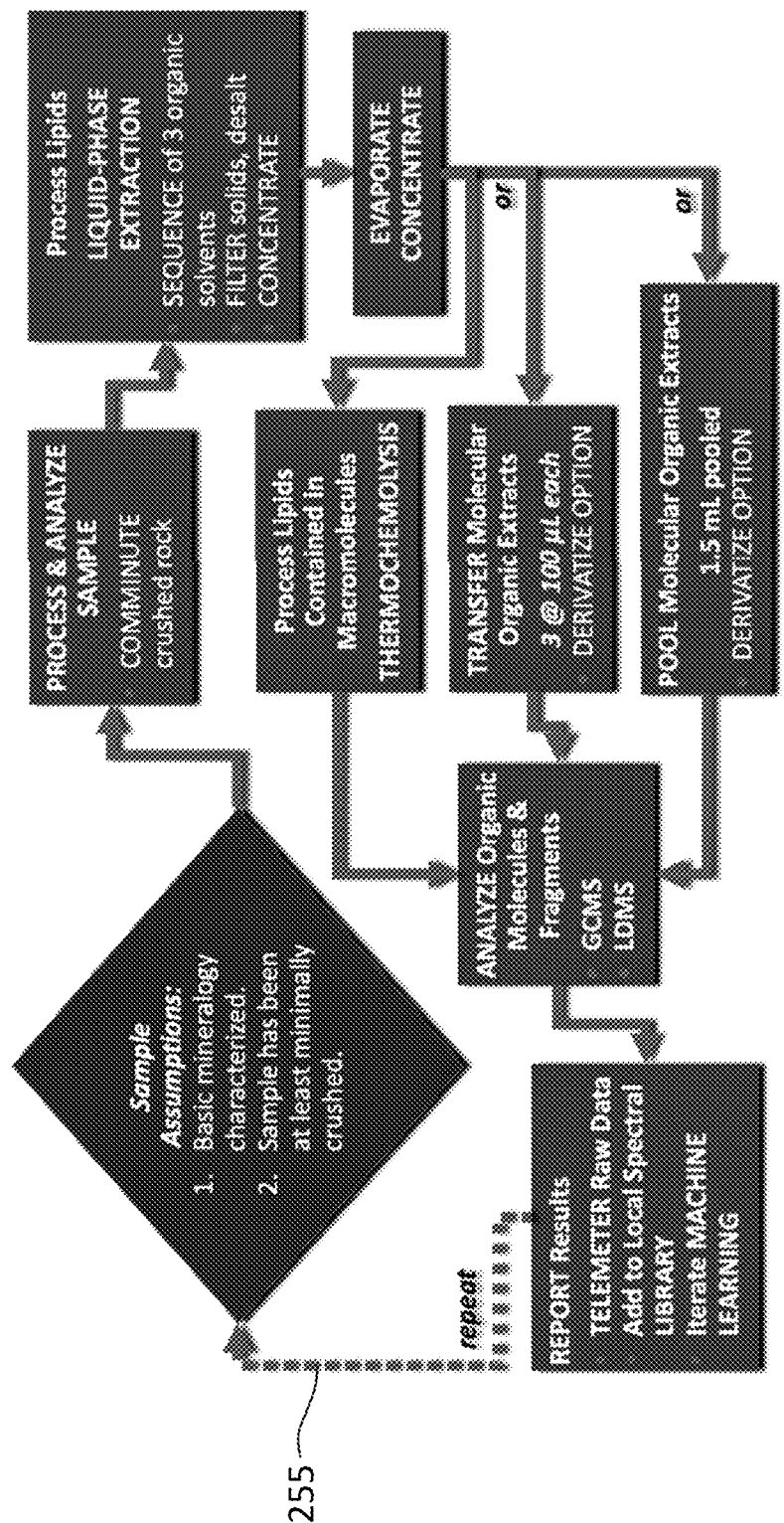
FIG. 10 is a flow diagram showing sample processing sequence and relationships of a system 100 in accordance with certain embodiments.

It will be appreciated that the sample processing sequence for lipid extraction is complex and consumable-intensive, and parameters vary depending on classes of lipids present. Machine learning algorithms 254 (FIG. 1) can be applied by controller 214 to adjust the processing steps and parameters governing the operation of extraction system 200. With additional reference to FIGS. 9 and 10, machine learning algorithms can provide iterative feedback at 255 (FIG. 10) to determine resource-efficient processing sequences to maximize extraction yield, for example. A body of knowledge (expert or experience data) relating to analysis decisions from trained and experienced experts, such as laboratory scientists and biochemists, can provide the training data for the machine learning algorithms 254. The machine learning algorithms shape the logic for the use of information collected from earlier samples to inform subsequent decisions. In certain embodiments, machine learning algorithms 254 select the most efficient processing steps to apply to subsequent similar samples. In this manner, an organic sample processing selection policy (e.g. solvent selection, step order and timing, subsequent analytical processes applied) is developed, and processing in extraction system 200 is adjusted, based on such policy feedback. This improves the operation of the extraction system 200, making it more efficient with the limited material and energy budgets available on flight missions or for other difficult to reach or access applications. In certain embodiments, this can also translate to more tests that can be performed and more data and information obtained with a given amount of material, time and energy.

In certain embodiments, the application of machine learning as described herein can be used to produce two policies:
1. The first is a setting of instrument parameters based on geological context of the sample to be ingested.
2. The second is a mapping from observations that will output either recommended instrument parameter settings for a secondary analysis, or the recommendation to take no further action with the current sample.

In certain embodiments, these policies may be implemented as neural networks, although other representations (e.g. decision trees, look-up tables) are possible, and can be tailored to the specific memory requirements of a mission.

In certain embodiments, the policies are trained using machine learning techniques from expert operation on real and simulated terrestrial samples, for example produced by a research team. While the policies are expected to be static in space mission scenarios, in certain embodiments they can also be updated in situ using reinforcement learning (RL) techniques, for example if the system is provisioned with a mission-specific reward function. One application is the use of these RL/ML techniques to make an instrument that can, when permitted, optimize its own operating parameters, as well as the specification of the reward function.

In certain embodiments, the system may be equipped with an algorithm that will integrate evidence from repeated observations about the diagnostic origin of the system. The algorithm used may include a Bayesian filter over a multinomial distribution. The probability distributions can be designed based on models of how observable quantities map to the probability of the observation coming from a sample of a specific diagnostic origin. These distributions can be learned from data collected and labelled by a research team of experts.

As will be appreciated, there are a number of proposed lifesigns in astrobiology, and it may be important, when designing a mission, to assess the quality of different lifesigns. Machine learning algorithms described herein can be applied for this purpose.

Using a Bayesian framework, an assessment of how likely an observation of a biomarker is to change our belief in whether or not a sample is of biotic or abiotic origin can be made. To accomplish this, we need a model of how likely an observation, z, for a biomarker i is, given the diagnostic origin of the sample. We quantify how likely the observation is to change our beliefs by looking at the likelihood ratio:

$$\lambda_i(z) = \frac{P(Z^i = z | O = A)}{P(Z^i = z | O = B)}$$

The quantity $\lambda_i(z)$ is proportional to the Bayes Factor, which informs how much one's beliefs are updated after the observation z. We can use the quantity $\lambda_i(z)$ to make choices between different lifesigns, given the likelihood of the different observations.

$\lambda_i(z)$ is contained in the range $[0, \infty[$, with the key decision point being $\lambda_i(z)=1$. If $\lambda_i(z)<1$, then biotic origin is more likely. If $\lambda_i(z)>1$, abiotic origin is more likely. If $\lambda_i(z)=1$, then the two hypotheses are equally likely.

We can consider a number of different ways of assessing the quality of a biomarker over its observation space, depending on a number of different mission factors. If we have unlimited sampling resources, we may want to consider the maximum shift in belief over all the observation space. With limited resources we may want to choose the biomarker(s) that maximize the minimum change in belief. If we have knowledge over the expected frequency of the observation space, we may want to consider the average performance. However, in this last case it is not sufficient to take the expectation of $\lambda_i(z)$ directly. In this case we should consider the quantity $|\log \lambda_i(z)|$, which does not detract from the analysis. Where the decision space for $\lambda_i(z)$ are the ranges $[0, 1[$ (biotic), and $]1, \infty[$ (abiotic), for $\log \lambda_i(z)$ the decision ranges are $]-\infty, 0[$ (biotic), and $]0, \infty[$ (abiotic).

For our purposes we will consider the expectation over the observation space. We will determine the quality of biomarker i, denoted $Q_{avg}(i)$, as $$Q_{avg}(i) = E_{Z^i}[|\log \lambda_i(z)|]$$

Figure 11:
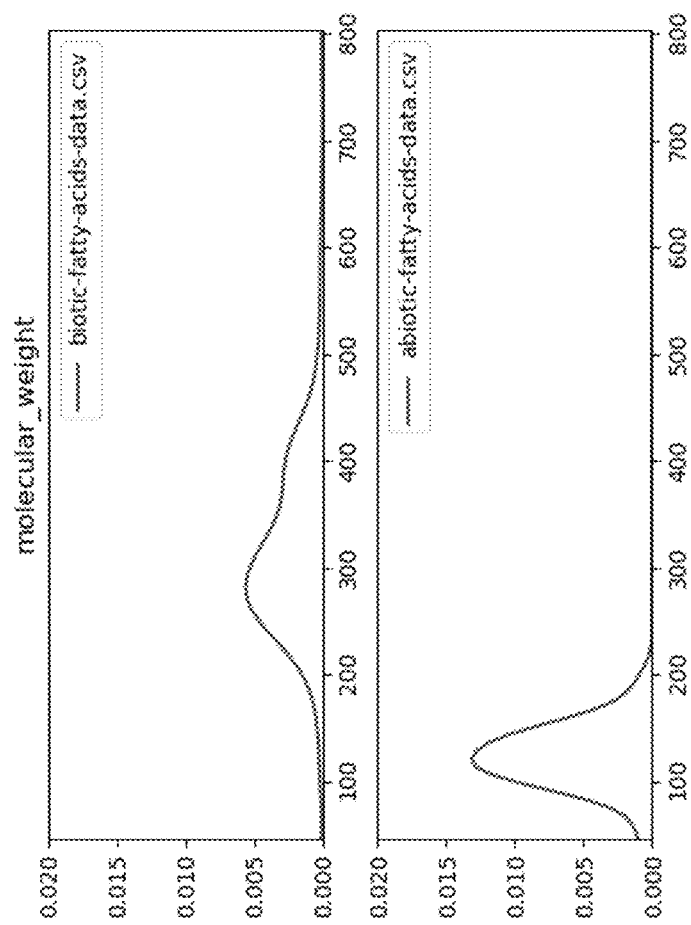
FIG. 11 is a plot of a probability distribution over the molecular weight of fatty acids.

As an example, consider the molecular weight of lipids, with collected data on fatty acids. FIG. 11 gives an example of a probability distribution over the molecular weight of fatty acids. It shows a kernel density estimator (KDE) using Gaussian kernels of the molecular weight of fatty acids. The maximum molecular weight values we sampled range from 0 to 800. The top plot shows $P(Z|O=B)$, and the bottom plot shows $P(Z|O=A)$.

We have selected a range (or set) of possible values the life signature can take on, and for each value, z, we can compute $P(Z=z|O=A)$ and $P(Z=z|O=B)$.

$$Q_{avg}(i) = \int_{z \in Z^i} \left| \log P(Z^i = z | O = A) - \log P(Z^i = z | O = B) \right| dz$$

The input space can take on continuous values, so it makes sense to use a sampling strategy to compute the integral above. This is the approach taken in Algorithm 1 below. With these values it becomes possible to compute the expectation of the value of the life sign. The algorithm is as follows:

---
Algorithm 1: Compute life sign utility.

---
Inputs: Observation space, Z, Abiotic Probability Model (e.g. the KDE from above), $f_A(z)$, Biotic Probability Model (e.g. the KDE from above), $f_B(z)$.
Output: Expected utility (a number in $[0, \infty[$)
result ← 0
for z ∈ Z:
   result ← result + $|\log f_A(z) - \log f_B(z)|$
return result / $\|Z\|$

---

Figure 12:
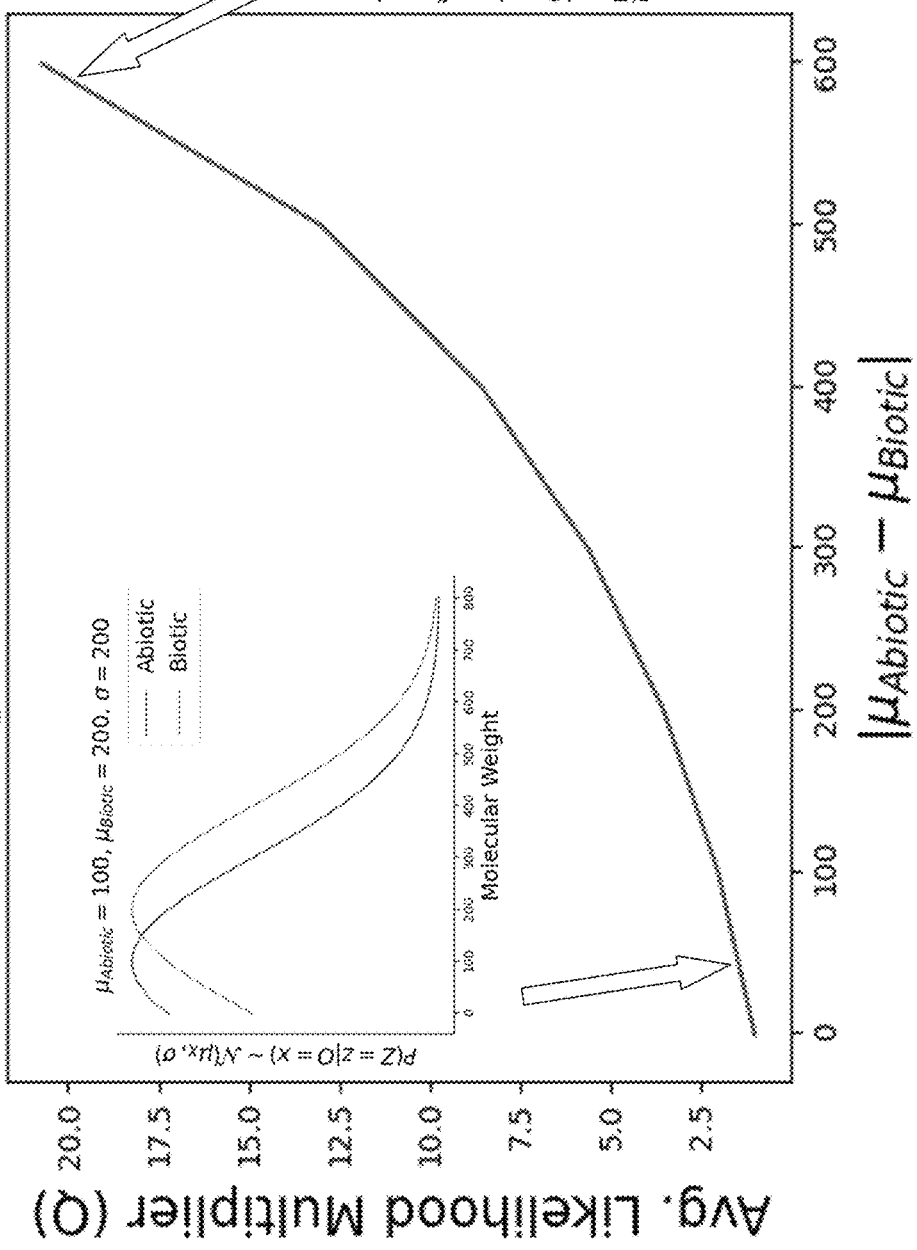
FIG. 12 is a plot of a simple distribution over the molecular weight for each class of materials (Abiotic and Biotic) as Gaussian Distributions.

FIG. 12 is a plot of a simple distribution over the molecular weight for each class of materials (Abiotic and Biotic) as Gaussian Distributions, both with a variance of 200, and with mean values in the range {100, 200, 300, . . . , 700}. The informativeness is computed and plotted, showing how much more informative a lifesign is as the biotic and abiotic distributions differ from each other.

It should be noted that the y axis in the main plot is the exponential of the value returned from Algorithm 1, just to make it a quantity that can be reasoned about more readily. An interpretation of it is "on average, an observation using this life sign is X-times more likely to come from one distribution rather than another." Knowledge gained in-mission can be used to update ranking of different potential lifesigns. Computing the expectation requires having an estimate of the probability of observing one of the readings from the different life signs, e.g. a particular molecular weight P(Z for a fatty acid, to keep i=z) consistent with the example. If we collect more data, we can update different distributions over potential observations, which will allow us to re-compute the $Q_{avg}(i)$ for the different life signs, and let us re-rank them in order to make future decisions about what instruments to deploy, or what different settings of the instrument to use.

In certain embodiments, a biotic/abiotic classification system based on machine learning techniques could be used to teach mobile robots how to direct sample acquisition. Further, as discussed above, in certain embodiments the system, using machine learning, can develop the ability to predict parameter settings for secondary processing of samples to maximize the lipid yield of individual samples. Based on prior observations, samples classified as biotic may warrant secondary processing using different processing parameters. Autonomously controlling the instrument for secondary observations increases the ability of the system to operate without human oversight, increasing mission autonomy, enabling operations in regions with limited communications, which may be critical for future missions to Icy Worlds. This capability could also aid in terrestrial or meteorite science in increasing the understanding of the origin of organic molecules contained in samples of interest.

Figures 8, 9:
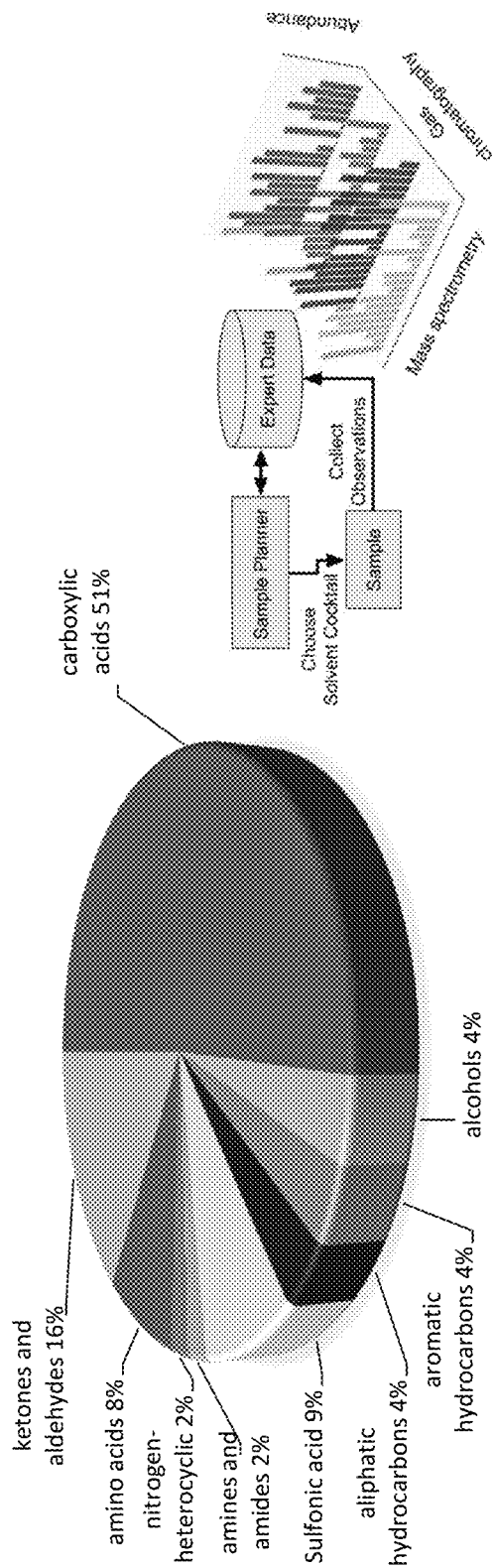
FIG. 8 is pie graph showing the lipid group distribution in Murchison Meteorite.
FIG. 9 a schematic diagram showing the use of machine learning in determining solvent cocktail based on models of expert data, in which results from mass spectrometry are used to update the decision-making model for future sampling stages.

Lipids are a diverse class of organic molecules that are broadly defined by their solubility in non-polar solvents (Ratnayake and Galli, 2009). On Earth, lipids make up the cell membranes of all known organisms, playing a key role in enabling cellular life (e.g. Georgiou and Deamer, 2014). They are also an energy source for organisms and facilitate transport of other biomolecules into and out of the cell (e.g. Georgiou and Deamer, 2014). While the majority of lipids on Earth are synthesized by biotic systems, they can also be formed abiotically, and are the most abundant organics found in carbonaceous chondrites and a likely major source of prebiotic organic molecules on both Earth and Mars (e.g., Sephton, 2005; Aponte et al., 2011; Remusat, 2014). As seen in FIG. 8 from Remusat (2014), the lipid groups carboxylic acids, aromatic and aliphatic hydrocarbons comprise almost 60% of soluble organics in Murchison Meteorite (a "type" example of a carbonaceous chondrite). Meteoritic lipids are likely a major source of organic matter deposited on early Earth and Mars during the Late Heavy Bombardment period.

TABLE 1

Differences in molecular structural patterns and features diagnostic of origin (biotic vs. abiotic) observed in the example of fatty acids, a major class of lipids.

| Origin-Diagnostic Pattern/Feature | BIOTIC: Terrestrial Fatty Acids | ABIOTIC: Fatty Acids found in Meteorites |
|---|---|---|
| Maxima and Distribution of Chain Lengths | Maxima at chain lengths longer than 12 carbon atoms, typically occurring at chain length 16 or 18. Unimodal distribution of chain lengths between chain lengths of 10 to 24 carbons. | Maxima at chain lengths of 1 or 2 carbon atoms. Poisson distributions in chain lengths between chain lengths of 2 to 12 carbons |
| Carbon Chain Abundance | Even chain lengths typically more abundant than odd chain lengths. Less often, odd chain lengths more abundant than even chain lengths. | No significant odd/even abundance differences |
| Branching Features in the Hydrocarbon Chains | Isomeric predominance of fatty acids with methyl branches at the iso or anteiso position; i.e. with a single $CH_3$ substituent at the penultimate or antepenultimate position in the chain opposite the carboxyl end | High isomeric diversity with many possible branched species and no preference for iso or anteiso methyl branched compounds |
| Unsaturations in the Hydrocarbon Chain | Between 1-6 unsaturations present on hydrocarbon chain. The most abundant unsaturated chain lengths are typically 16 or 18 carbons long | Unsaturations rarely reported, never more than 1 unsaturation in carbon chain |
| Presence of cyclic moieties | Cyclic moieties sometimes present on chain lengths of 15, 17, or 19 carbons | None reported |
| Abundance of cis vs. trans isomers | Cis conformer in excess | Trans conformer in excess |

Origin-Diagnostic Molecular Features in Lipids: Because lipids can be generated by both biotic and abiotic processes, they contain origin-diagnostic molecular features and patterns (e.g., Miβbach et al., 2018). Some of these features include chain length, position and number of unsaturations and branch points, presence of cyclic moieties and functional groups, and molecule conformation/isomerization (e.g., Lovelock, 1965; Eigenbrode, 2008). Examples of biotic and abiotic origin-diagnostic molecular features/patterns (Table 1) can reveal if a group of detected lipid molecules was synthesized via biotic or abiotic processes. Origin-diagnostic patterns and distributions in lipids extracted from biotic (i.e., terrestrial) and abiotic (i.e., meteoritic, see FIG. 2, and lab-synthesized) specimens are well-established in the literature (Cronin and Chang, 1993; Pizzarello et al., 2001; Summons et al., 2008; Eigenbrode, 2008; Georgiou and Deamer, 2014; Miβbach et al., 2018). Table 1 shows the origin-diagnostic features in the different groups of fatty acids, a major class of lipids. These features are distinguishable by system 100, implementing solvent extraction using extraction system 200 and gas chromatography-mass spectrometry (GC-MS) analysis using analysis system 400. For example, fatty acids synthesized by biotic systems display an even over odd chain length preference that peaks around $C_{16}$ or $C_{18}$, whereas abiotically synthesized fatty acids are typically much shorter, with chain lengths ranging from $C_1$-$C_{12}$ and peaking around $C_1$ or $C_2$ in a Poisson distribution. In addition to fatty acids, other classes of lipids (e.g., n-alkanes, polycyclic compounds) display numerous additional origin-diagnostic patterns, including presence/positioning of double bonds, presence of cyclic moieties in chains, and molecular conformation preferences. Understanding these patterns and features informs the application of the system 100 to the analyses of expected lipid distributions in samples from life detection targets, such as Mars.

Geologic Longevity of Lipids: Lipids are geologically robust: they have high preservation potential and can persist in the terrestrial geologic record for billions of years, an order of magnitude longer than any other biomolecule (e.g. Eigenbrode et al., 2008). Due to their longevity, preserved lipids may be one of the best indicators of past life in the search for evidence of life on Mars. Additionally, extremely arid conditions, like those on Mars over the last ~3 billion years, are expected to enhance structural preservation, especially in the absence of significant geothermal heating associated with burial, which is responsible for the vast amount of post-deposition alternation of organics on Earth (Wilhelm et al., 2017). Although Mars' surface receives more radiation than Earth's, burial with regolith can shield organics, preventing or slowing radiolytic degradation over geologic timescales. Estimates vary on the burial depths required for effective radiation shielding, but research suggests that ~10 cm (low estimate) to ~2 meters (high estimate) of overlying material can shield organics for relevant timescales (Osman et al., 2008; Moores and Schuerger, 2012; Pavlov et al, 2012; Eigenbrode et al., 2015; Fox et al., 2019). Numerous field-tested planetary drills can drill to these depths to acquire unaltered or minimally-altered material (Bar-Cohen et al. 2009) and without destroying lipids (Dave et al., 2018).

Organics Previously Detected on Mars: Organics are known to exist on Mars, and current understanding of the Martian organic inventory comes from studies of Martian meteorites (Steele et al., 2012; Lin et al., 2014; Steele et al., 2016; Jaramillo et al., 2019) and in situ discoveries, primarily from the 1975 Viking landers and 2012 Mars Science Laboratory (MSL) Curiosity rover. MSL's Sample Analysis at Mars (SAM) instrument suite discovered chlorinated hydrocarbons (Freissinet et al., 2015) and hydrocarbons likely derived from macromolecular organic matter in the ancient lake sediments of Gale crater (Eigenbrode et al., 2018). These detections highlight the potential for hydrocarbon preservation over several billion years on Mars, even after $10^5$-$10^6$ years of exposure to ionizing radiation (e.g., Benner et al., 2000; Fox et al., 2019). If life did not arise on Mars, lipids are still expected to remain on the surface/subsurface, sourced from extraplanetary organic material delivered by meteorites and interplanetary dust particles (see summary in Mahaffy et al., 2012) and/or endogenous compounds generated in-situ (e.g., through electrochemical reduction of $CO_2$) (Steele et al., 2018). The origin-diagnostic lipid analysis enabled by system 100 will help elucidate the astrobiological history of samples analyzed on Mars.

Mars is one of the most promising life detection targets in the Solar System, and in the search for evidence of life on Mars, preserved organic matter may be one of the best indicators of life. The arrangement described herein enables a reference mission to investigate biological and abiological sources of organic matter in ancient Martian sediments for preserved molecular signs of life. The reference mission seeks to distinguish between those sources and assumes that if life existed on ancient Mars, sedimentary records of habitable environments that also support accumulation and preservation would likely host diagnostic indicators of past life. This mission targets a site of optimal organic accumulation and preservation, focusing on (1) development of front-end sample-acquisition and preparation techniques that best conserve origin-diagnostic molecular structures/patterns, (2) analytical techniques customized for biomarkers with highest preservation potential in sedimentary deposits, and (3) discrimination of biogenic and abiogenic lipid signatures.

Mission Goal: The reference mission goal is to determine if life arose on Mars (Table 2) by interrogating ancient Martian sedimentary deposits to characterize the presence and structures of preserved, ancient lipids. To achieve this, system 100 adapts best-practice laboratory methods for lipid analysis, overcoming analytical challenges like low organic abundance, interference of minerals/salts, and degradation of origin-diagnostic molecular structures. Critically, these techniques reveal origin-diagnostic information, whereas non-solvent/pyrolytic-based techniques obscure or destroy molecular structures. Solvent extraction also mitigates detection ambiguities and maximizes signal-to-noise ratio.

Sample Input Assumption: System 100 can accept samples acquired by a drill. In certain embodiments, to mimic drilled rock found on Mars, loose soil simulants that match the mineralogical composition found on Mars (Vaniman et al., 2014) can be used to ensure realistic evaluation and operation of system 100. Sample mineralogical composition and hardness can affect the viscosity of the solvent-particulate slurry, particle-size distribution post-comminution, and electrostatic properties of the slurry. These chemical and physical properties significantly impact design considerations for system 100. The mineralogy of mudstone on Mars includes silicates, including smectite and plagioclase (Vaniman et al., 2014). Exolith MGS-1C Clay ISRU, composed of 40% smectite and 16.4% plagioclase (Cannon et al., 2019) can be used as a soil simulant due to its mineralogical similarity to Martian mudstone; it can be used to test the comminution and filtration capabilities of the extraction system 200 and to investigate the behavior of the solvent-particulate slurries during extraction.

Some other Potential Applications: It is worth noting that system 100 may also be deployed on other planetary surfaces with simple modifications to extraction parameters such as solvent polarity, temperature and pressure. For example, soluble $C_1$-$C_{10}$ carboxylic acids could be potentially preserved in volatile-rich regions on the Moon (e.g., permanently shadowed regions) or other carbonaceous bodies. System 100 can also be modified to accept ice-rich samples from life-detection targets such as Europa and Enceladus.

Further, as mentioned above, system 100 can be used to detect lipids in Earth soil to determine presence of petrochemicals for example, to detect oil spills or other contaminations, or for purposes of exploration. In certain embodiments, for instance, the system 100 be integrated into benchtop analysis or onto an unmanned terrestrial rover for field exploration. Additionally, since system 100 receives the sample from an external component (e.g. a drill), it could conceivably be integrated into an aquatic system for petroleum studies with only minor modifications.

It should also be noted that while the described applications are for extraction of lipids biomarkers using non-aqueous solvents, the extraction of lipids is by no means a limitation. The extraction and concentration techniques from rock/soil samples described herein can be applied to any biomarkers by changing the solvent (water can also be used, but probably not strong acids or bases), temperature and agitation. This may require routine changes to the operating specifications and procedures, but not the overall design of the instrument. The only step that is lipid specific is the derivatization which can be eliminated or modified as necessary.

It should also be noted that adaptation of system 100 to other applications would generally entail modification of the extraction system 200, without necessarily modifying analysis system 400, which in all cases may be a separate component from the extraction system and may be located remotely from the extraction system and deployed for its analysis purposes at a later time than the extraction system.

In certain embodiments, the system 100 can be used to help determine four primary science goals: (1) Determine if life ever arose on Mars; (2) Explore the geochemical history and evolution of Mars (i.e., elucidate oxidizing/reducing conditions during burial that led to preservation, potentially identify lipid-generating hydrothermal activity); (3) Understand the primordial sources of organics on Mars; (4) Understand where organic synthesis continues today. These goals are directly responsive to the 2014 NASA Science Plan, 2013-2022 NASA Planetary Science Decadal Survey, and the MEPAG science goals for exploration of Mars. To accomplish these goals the system 100 may be used to isolate a range of lipids in three classes (i.e., fatty acids, alkanes, cyclic compounds) while using thermochemically mild techniques to preserve the origin-diagnostic molecular features that provide valuable information about a sample's biogenicity and geologic history. Table 2 shows a science traceability matrix mapping larger mission science goals and objectives to engineering requirements.

TABLE 2

| Science Goals | Science Objectives | Investigation/ Observables | Measurement Requirements | | Projected Performance |
|---|---|---|---|---|---|
| | | | ExCALIBR-Accessible Parameters | ExCALIBR Requirements | |
| Determine if life ever arose on Mars [1,2] | Biotic vs. abiotic: analyze origin-diagnostic molecular features of individual lipid molecules on Mars to constrain synthesis conditions Characterize distributions of origin-diagnostic molecular features in Martian lipid profile as biotic or abiotic | Detailed inventory of lipid organics in returned samples, including: (a) identify individual compounds (b) identify molecular features | Extracted, concentrated lipids for analysis (including those with cyclic/aliphatic moieties) from rock or regolith. Non-destructive | (1) Accept 50 g sample acquired with a drill or scoop (2) Support multiple extraction solvents (3) Lose <10% of extracted lipids [$C_4$-$C_{30}$ alkanes | (1) Adaptable to front end sample acquisition system (2) Compatible with dichloromethane, methanol, and hexane (3) Total lipid loss to system <20% |

TABLE 2-continued

| Science Goals | Science Objectives | Investigation/ Observables | ExCALIBR-Accessible Parameters | ExCALIBR Requirements | Projected Performance |
|---|---|---|---|---|---|
| Explore the geochemical history & evolution of Mars [3,4] | Use chemical information from preserved molecular structures to understand geochemical conditions during burial on Mars | (weight & composition, functional groups, geometric conformation/ isomerization) (c) quantify total and individual classes of lipids (d) determine relative lipid abundances | method preserves origin-diagnostic molecular structures/ patterns: molecular weight, branch points, un-saturations, functional groups, molecular conformation. | & $C_1$-$C_{30}$ fatty acids] (4) Preserve >75% of origin-diagnostic structures (5) Extract at temperatures of 0-200° C. (6) Concentrate lipids ≥ 1000x (7) Recover $C_4$-$C_{30}$ alkanes present at ≥1 pg (1 ppt) with 75% efficiency | (4) >90% of diagnostic structures preserved (5) Temp range 0-120° C. ± 3° C. accuracy (6) Solvent volume concentrated from 250 ml to 100 UL (7) 80% extraction efficiency for 1 pg of $C_4$-$C_{30}$ alkanes in 1 g of sample |
| Understand the primordial sources of organic matter [5] | Identify ancient Martian lipids, investigate preservation history relative to mineral matrix & geologic environment | | | | |
| Understand where organic synthesis continues today [5] | Elucidate how, where, & which modern Martian lipids are synthesized | | | | |

Laboratory techniques for lipid analysis have been used on terrestrial samples for over 70 years and are effective at overcoming common challenges associated with analysis of natural, complex organic material preserved in soils and rock. Though well established, these techniques are laborious, operator dependent, and require consumables, previously precluding in-situ analysis. Flight heritage techniques for lipid detection are operationally simple, and have been successful in identifying small, simple hydrocarbons on Mars (e.g., Eigenbrode et al., 2018), but these high-temperature thermal extraction techniques (i.e., pyrolysis) destroy detailed origin-diagnostic molecular patterns and features. For example, pyrolysis-GC-MS can determine the presence of organic fragments but cannot reliably detect whole molecules or ascertain patterns in chain lengths, double bonds, branch points, or isomerization patterns.

To improve upon current flight techniques for lipid extraction, system 100 performs non-destructive lipid sample processing within the low mass and power budgets required for flight. The system processes samples in situ, integrating laboratory extraction steps on a small scale to minimize reagent volumes and concentrate organics for analysis, increasing detection signal by almost three orders of magnitude, as summarized in Table 3 below, in which the system 100 is referred to as ExCALiBR. In certain embodiments, the system (1) accepts a ~50 gram drilled/scooped sample of regolith/rock/ice (the current drill designed for Mars 2020 would be capable of providing our sample input), (2) comminutes the sample under vacuum to reduce grain size and liberate organics from the mineral matrix, cold-trapping any released volatile organics for evolved-gas analysis while also dehydrating, (3) extracts organics with a series of organic solvents and a sonic probe, (4) filters particulate matter from the lipid analyte, (5) evaporates solvent to concentrate the ~250 mL sample to (near) dryness, and (6) makes the extract available for downstream analytical instruments, by one or more of (a) transfer in a stream of heated carrier gas of readily volatilized compounds, (b) redissolution in a defined solvent volume, or (c) transfer of the collection vessel to the analytical system. These sequential processing steps are performed to extract lipids without destroying them or altering origin-diagnostic features before analysis.

TABLE 3

| System Performance Parameter | Requirement |
|---|---|
| Number of Samples | 1.1 ExCALIBR shall be capable of analyzing 3 unique samples and 1 control |
| Sample Acquisition | 1.2 ExCALIBR shall accept a sample from a drill |
| Sample Size | 1.3 ExCALIBR shall be capable of processing a sample size of 50g +− 10% |
| Number of Solvents | 1.4 ExCALIBR shall maintain a maximum of 4 organic solvents |
| Solvent Volume | 1.5 ExCALIBR shall maintain a maximum volume of 1000 mL, and (concentrated) minimum |
| Compatibility with Non-Aqueous (Organic) Solvents | 1.6 The amount of leached containments in blank run shall be < ppb using 5:1 V/V dichloromethane to methanol |
| Conservation of Origin-Diagnostic Molecular | 1.7 ExCALIBR shall maintain a <5% loss of lipid structures |
| Sample Residue Removal | 1.8 ExCALIBR shall remove >95% of soil particles from solvent phase with retention of >95% of solvent |
| Organics Separation | 1.9 ExCALIBR shall maintain a loss of no less than ⅓ of original organics during separation |
| Output Particle Size | 1.10 ExCALIBR shall output no particles >0.5 μm |
| Concentration Factor | 1.11 ExCALIBR shall be able to concentrate sample by ~2000x |
| Analyte Lipid Peaks | 1.12 ExCALIBR shall maintain output lipid peaks above GCMS LOD |
| Instrument Power Usage | 1.13 ExCALIBR shall consume <300 Whrs/sample (Motors, Heaters, Sonicator, Valves) |
| Instrument Motors | 1.14 ExCALIBR shall maintain 1 × high power motor and 1 × lower power motor |
| Sample Sensors | 1.15 ExCALIBR shall maintain 12 × temperature sensor, 4 × pressure sensor, 1 × solvent |

TABLE 3-continued

| System Performance Parameter | Requirement |
| --- | --- |
| Surface Heaters | 1.16 ExCALIBR shall maintain surface heaters for the concentrator, extractor, and sample |
| Radiation Environment | 1.17 ExCALIBR shall be able to function in 25 krad +− 25% |
| Output Sample Size | 1.18 ExCALIBR shall output a sample size of 100 µL +− 25% |
| Contamination Control | 1.19 ExCALIBR shall both sterilize/kill microbes and remove organic and lipid contamination below analytical instrument LoD |

System 100 significantly increases chances of detecting organic indicators of life in an astrobiologically-significant sample on Mars. Currently, no single instrument exists that can perform lipid extraction with fidelity as high as benchtop laboratory extraction techniques. The SAM instrument suite on MSL used thermal extraction to liberate and volatilize organics (Mahaffy et al., 2012). While this technique is operationally simpler, high temperatures cause deleterious chemical reactions, especially in the presence of the soil oxidants (e.g. oxychlorine anions) ubiquitous on Mars (e.g., Navarro-Gonzales et al., 2010; ten Kate et al., 2010). Additionally, high temperatures can modify and obscure origin-diagnostic lipid patterns. These destructive reactions occur at negligible rates in the organic liquid phase, but resource constraints have previously precluded solvent extraction approaches on flight instruments (Mahaffy, 2008). By using liquid (solvent)-handling techniques as disclosed herein, origin-diagnostic lipid patterns are conserved and delivered unadulterated to an analytical instrument. System 100 actualizes science objectives by (1) conserving origin-diagnostic lipid structures/patterns by maintaining them in the liquid phase using organic solvents required for optimal lipid extraction, (2) reducing signal interference by extracting lipids from the mineral matrix and filtering out minerals, which are known to interfere with Mars sample analysis, (Mahaffy et al. 2012) and (3) increasing the concentration of lipids by ~2500× in the sample relative to initial extract volume. Concentrating the extracted sample ensures a sufficiently low LoD of origin-diagnostic ancient organics preserved on Mars (likely <ppb). Low biomass concentration is a common problem in the analysis of Mars analog samples (Bowden and Parnell, 2007; Wilhelm et al. 2018).

Example 1

A non-aqueous fluidic system 100 capable of extracting lipid biomarkers from planetary samples performs filtration of the resulting extract, and concentrating analytes for downstream analysis by analysis system 400. Extraction system 200 successfully extracted both concentrated lipid standards and a natural sample (1 g of Atacama Desert surface soil, a Mars analog) with a 1:5 v/v ratio of sample to solvent (9:1 v/v dichloromethane methanol (DCM): methanol (MeOH)). Mineral residue was filtered out using a filter 200 comprising a sintered stainless-steel frit (pore diameter 0.5 µm). Extracts containing lipid analytes were vacuum-concentrated to dryness, leaving only the dry extracted lipids on a collection disk (not shown) at the bottom of the concentrator 240. The collection disk was removed from the system, then dried lipids were re-solubilized and analyzed via commercial benchtop in a gas chromatographer-mass spectrometer (GC-MS) (not shown).

Example 2

A system 100 includes four units: comminutor, extractor, filter, and concentrator integrated into an all-in-one design. The approximate dimensions of the system are 112 cm tall and 36 cm in diameter (at widest point). It accepts a sample size of about 50 g, solvent volume of about 250 mL, and processes three samples and one system blank. In one application the sample is 50 g sample of Mars-analog sample (Exolith clay) which is transferred to the comminutor-extractor unit 104. Particles are broken down via a blender-style comminutor 204. Organic solvents are then introduced, and lipid extraction performed with a custom sonicator 208 that periodically agitates and disperses solids, forming a slurry. Solvent and regolith are then transferred to a 3-stage filter stack 222 that isolates the lipid-containing analyte from the regolith. A concentrator 240 reduces the analytic solution to 100 µL under Martian atmospheric pressure (6-10 Torr). The remaining lipid analyte is transferred to an analytical instrument, nominally a GC-MS. Extraction of multiple benchmarking lipid standards ($C_{19}$ n-alkane, $C_{16}$ fatty acid methyl ester) and a natural sample (1 g of Atacama Desert surface soil, a Mars analog) was demonstrated laboratory. Extraction was confirmed by GC-MS analysis for ~1 g samples of Atacama Soil in 5 mL of solvent. Separately, highly effective stirring of solvent, including suspension of the entirety of a 50 g reference clay sample (Exolith simulant, see section 1.2.2.3) in ~250 mL of DCM, was demonstrated.

Example 3

Comminutor Unit: the effective reduction of particle size to the target, i.e. predominantly <50 µm for >75% of particles, has been demonstrated for a number of reference samples (Exolith Mars analog reference soil and Atacama Desert surface soil with initial particle-size distribution centered around 18.52 µm) using a compact design comminutor 204 that utilizes a 50-mm-long, hardened metal impeller rotating at 28,000 rpm to reduce average particle size of minerals; size reduction depends on both particle characteristics and the time of operation of the impeller. After one minute of comminution using this device, particle-size analysis revealed that 40.74% of the particle size distribution was <10 µm.

Example 4

Extractor with ultrasonic agitation of solvent: Extraction of multiple benchmarking lipid standards ($C_{19}$ n-alkane, $C_{16}$ fatty acid methyl ester) and a natural sample (1 g of Atacama Desert surface soil, a Mars analog) was demonstrated using extraction system 200. Extraction was confirmed by GC-MS analysis for ~1 g samples of Atacama Soil in 5 mL of solvent. Separately, highly effective stirring of solvent, including suspension of the entirety of a 50 g reference clay sample (Exolith simulant, see section 1.2.2.3) in ~250 mL of DCM, was demonstrated.

Example 5

Filter Unit: Using a filter 220 (sintered stainless-steel frit, nominal pore diameter 0.5 µm); mass loss of the filtrate after evaporation to dryness of the filtrate was negligible (<1 mg).

Example 6

A concentrator 240 uses a simple stainless-steel disk at the bottom to capture lipids, as solvent is removed under vacuum, for subsequent analysis. The sample-capture disk served as a representation of the bottom of a sample cup 242 or disk similarly located in the system 200, the design of which accounts for transfer of the entirety of the collector itself (if a disk), or of the lipids volatilized in an inert carrier gas stream, to a GC, MS, GC-MS, or LDI-MS for analysis.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted based on the foregoing description. This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

What is claimed is:

1. A single instrument integrated non-aqueous fluidic system for extracting, filtering and concentrating lipid biomarkers from planetary samples, wherein the single instrument integrated non-aqueous fluidic system comprises:
    a sample input unit for receiving a sample;
    a solvent vessel configured to store one or more organic solvents;
    a combined comminution-extraction unit including:
        a container connected to the sample input unit, the sample input unit configured to introduce the sample into the container, wherein the sample is introduced through the sample input unit,
        a solvent port disposed between the container and the solvent vessel wherein the solvent port is configured to introduce one or more organic solvents into the container from the solvent vessel for mixing with the sample, wherein the one or more organic solvents are introduced through the solvent port and whereby lipids can be extracted into an organic phase through the mixing of the one or more organic solvents with the sample,
        a comminutor configured to rotate in the container whereby at least 50% of the sample can be pulverized into a reduced particle size, and
        a sonicator configured to agitate the sample in the container whereby the sample in the container can be dispersed into the one or more organic solvents in the container and a solvent-sample slurry comprising a solvent phase can form in the container,
        wherein the sample input unit is vertically disposed above the container and wherein the solvent vessel is vertically disposed above the container;
    a filtration system in fluid communication with the container, wherein the filtration system comprises one or more filters operable to pass the solvent phase; and
    a concentrator in fluid communication with the filtration system, wherein the concentrator comprises an analysis assembly and is operable to receive the solvent phase from the one or more filters and to concentrate lipid extracts for analysis.

2. The single instrument integrated non-aqueous fluidic system of claim 1, wherein the filtration system comprises two or more filters arranged in a filter stack.

3. The single instrument integrated non-aqueous fluidic system of claim 2, wherein the reduced particle size is less than 10 µm.

4. The single instrument integrated non-aqueous fluidic system of claim 3, wherein the single instrument integrated non-aqueous fluidic system has a height from about 25 cm to about 120 cm, and a diameter from about 5 cm to about 40 cm.

5. The single instrument integrated non-aqueous fluidic system of claim 1, further comprising an analysis system configured to receive the lipid extracts, to perform analysis on the lipid extracts, and to report the results of the analysis.

6. The single instrument integrated non-aqueous fluidic system of claim 5, further comprising a controller configured to determine resource-efficient processing sequences and to maximize extraction yield by the extraction system by applying a machine learning algorithm, wherein the analysis system is configured to report results of the analysis to the controller.

7. The single instrument integrated non-aqueous fluidic system of claim 6, wherein the controller is programmed to determine the resource efficient processing sequences using the results of the analysis by applying the machine learning algorithm.

8. The single instrument integrated non-aqueous fluidic system of claim 5, wherein the analysis system comprises a gas chromatography-mass spectrometry instrument.

9. The single instrument integrated non-aqueous fluidic system of claim 5, wherein the analysis system comprises a laser-desorption-ionization mass spectrometry instrument.

10. The single instrument integrated non-aqueous fluidic system of claim 5, wherein the analysis system comprises a surface-enhanced Raman spectroscopy instrument.

11. The single instrument integrated non-aqueous fluidic system of claim 5, wherein the analysis system comprises a Raman spectroscopy instrument.

12. The single instrument integrated non-aqueous fluidic system of claim 5, wherein the analysis system comprises one of a gas chromatography-mass spectrometry instrument or a laser-desorption-ionization mass spectrometry instrument, and further comprises a surface-enhanced Raman spectroscopy instrument or a Raman spectroscopy instrument.

13. The single instrument integrated non-aqueous fluidic system of claim 1, wherein the sonicator is disposed in direct contact with an exterior surface of the container whereby sonic energy can be conducted through a wall of said container.

14. The single instrument integrated non-aqueous fluidic system of claim 1, wherein the comminutor is coupled to a motor exterior of the container using a single shaft penetrating the container through a hermetic shaft seal.

15. The single instrument integrated non-aqueous fluidic system of claim 1, further comprising one or more sensors for providing one or more temperature or pressure feedbacks.

16. The single instrument integrated non-aqueous fluidic system of claim 1, wherein the filtration system comprises two or more filters disposed in a carousel arrangement operable to rotate and seal one of the two or more filters at a time into operation.

17. The single instrument integrated non-aqueous fluidic system of claim 1, wherein the analysis assembly comprises a removable collection disk to collect and re-dissolve dry lipid extracts.

18. The single instrument integrated non-aqueous fluidic system of claim 17, wherein the removable collection disk is one of a plurality of disks disposed in a carousel arrangement operable to rotate and seal different collection disks into operation.

19. The single instrument integrated non-aqueous fluidic system of claim 1, further comprising a controller programmed to determine resource-efficient processing sequences and to maximize extraction yield by the extraction system by applying a machine learning algorithm.

20. The single instrument integrated non-aqueous fluidic system of claim 19, wherein the machine learning algorithm is programmed to determine the resource-efficient processing sequences by using data collected from training samples and expert data.

21. The single instrument integrated non-aqueous fluidic system of claim 1, wherein the sample input unit is configured to receive an unprocessed planetary sample comprising regolith, rock powder, or icy materials.

22. The single instrument integrated non-aqueous fluidic system of claim 1, wherein the filtration system is detachably attached from above and directly to the concentrator.

23. The single instrument integrated non-aqueous fluidic system of claim 1, wherein the concentrator further comprises a vent and a vacuum concentrator.

24. The single instrument integrated non-aqueous fluidic system of claim 1, further comprising at least:
   a membrane;
   a seal; and
   a housing; wherein the membrane, the seal and the housing each comprise materials compatible with dichloromethane methanol.

25. The single instrument integrated non-aqueous fluidic system of claim 14, wherein the comminutor comprises a blade coupled to the single shaft and is further configured to mix the one or more organic solvents with the sample in the container.

* * * * *